United States Patent
Stejskal et al.

(10) Patent No.: US 9,958,403 B1
(45) Date of Patent: May 1, 2018

(54) ARRANGEMENT FOR X-RAY TOMOGRAPHY

(71) Applicant: FEI Company, Hillsboro, OR (US)

(72) Inventors: Pavel Stejskal, Brno (CZ); Marek Unčovský, Brno (CZ); Tomáš Vystavěl, Brno (CZ); Alan Frank de Jong, Eindhoven (NL); Bart Buijsse, Eindhoven (NL); Pierre Bleuet, Grenoble (FR)

(73) Assignee: FEI Company, Hillsboro, OR (US)

( * ) Notice: Subject to any disclaimer, the term of this patent is extended or adjusted under 35 U.S.C. 154(b) by 0 days. days.

(21) Appl. No.: 15/728,252

(22) Filed: Oct. 9, 2017

(30) Foreign Application Priority Data

Oct. 11, 2016 (EP) .................................... 16193273
Nov. 3, 2016 (EP) .................................... 16197127

(51) Int. Cl.
*G01N 23/00* (2006.01)
*G01N 23/04* (2018.01)
*G21K 7/00* (2006.01)

(52) U.S. Cl.
CPC ..... *G01N 23/046* (2013.01); *G01N 2223/401* (2013.01); *G01N 2223/419* (2013.01); *G21K 7/00* (2013.01)

(58) Field of Classification Search
CPC ........... G01N 23/046; G01N 2223/401; G01N 2223/419; G21K 1/00
See application file for complete search history.

(56) References Cited

FOREIGN PATENT DOCUMENTS

| EP | 2903398 | 8/2015 |
|---|---|---|
| JP | 2011-007766 | 1/2011 |
| JP | 2012-022922 | 2/2012 |
| WO | WO 1998/045853 | 10/1998 |
| WO | WO 2014/174997 | 10/2014 |
| WO | WO 2016/086908 | 6/2016 |

OTHER PUBLICATIONS

Extended European Search Report mailed by the European Patent Office dated Apr. 12, 2017, for EP App. No. 16197127.0.

(Continued)

*Primary Examiner* — Dani Fox
(74) *Attorney, Agent, or Firm* — Klarquist Sparkman, LLP (57) ABSTRACT

A method of investigating a specimen using X-ray tomography, comprising (a) mounting the specimen to a specimen holder, (b) irradiating the specimen with a beam of X-rays along a first line of sight through the specimen, and (c) detecting a flux of X-rays transmitted through the specimen and forming a first image. Then (d) repeating the steps (b) and (c) for a series of different lines of sight through the specimen, thereby producing a corresponding series of images. The method further comprises (e) performing a mathematical reconstruction on said series of images, so as produce a tomogram of at least part of the specimen, wherein the specimen is disposed within a substantially cylindrical metallic shell with an associated cylindrical axis, the beam of X-rays is produced by directing a beam of charged particles onto a zone of said metallic shell, so as to produce a confined X-ray source at said zone, and the series of different lines of sight is achieved by rotating said shell about said cylindrical axis, thereby causing relative motion of said zone relative to the specimen.

20 Claims, 4 Drawing Sheets

(56) References Cited

OTHER PUBLICATIONS

Extended European Search Report mailed by the European Patent Office dated Mar. 17, 2017, for EP App. No. 16193273.6.
Ishino et al., "Development of a specimen holder combined with ultra thin film laser plasma x-ray source for compact contact-type soft x-ray microscope to observe hydrated living biological cells," Proc. of SPIE 8139:81390R-1 to 81390R-8 (2011).
Neuser et al., "nanoCT(R) Visualizing internal 3D structures with submicrometer resolution," International Symposium on Digital Industrial Radiology and Computed Tomography, Jun. 27, 2007, available at: http://www.ndt.net/article/dir2007/papers/24.pdf (accessed Mar. 7, 2017).
Colin M. Palmer, "A cylindrical specimen holder for electron cryo-tomography," Doctoral Dissertation, University of Cambridge, Sep. 2012 (118 pages).
Perini et al., "Towards laboratory X-ray nanotomography: instrumental improvements on a SEM-based system," Proc. of SPIE 99671:99671A-1 to 99671A-7 (2016).
Ryan et al, "Specimen holder design for X-ray microanalysis of thin films in the TEM: reduction of spurious X-rays," Journal of Microscopy 134:281-289 (1984).
Notice of Reason(s) for Rejection in Application No. JP2017-196495 from the Japanese Patent Office, dated Dec. 5, 2017 (with English translation).

ARRANGEMENT FOR X-RAY TOMOGRAPHY

CROSS REFERENCE TO RELATED APPLICATION

This application claims priority to European Patent Application No. EP16193273.6, filed Oct. 11, 2016, and European Patent Application No. EP16197127.0, filed Nov. 3, 2016. The entire disclosures of each of European Patent Application No. EP16193273.6 and European Patent Application No. EP16197127.0 are incorporated herein by reference.

SUMMARY

The disclosure relates to a method of investigating a specimen using X-ray tomography, comprising (a) mounting the specimen to a specimen holder; (b) irradiating the specimen with a beam of X-rays along a first line of sight through the specimen; (c) detecting a flux of X-rays transmitted through the specimen and forming a first image; (d) repeating steps (b) and (c) for a series of different lines of sight through the specimen, thereby producing a corresponding series of images; and (e) performing a mathematical reconstruction on the series of images, so as to produce a tomogram of at least part of the specimen.

In tomographic imaging (also referred to as Computed Tomography (CT)) as referred to above, the source and (diametrically opposed) detector are used to look through the specimen along different lines of sight, so as to acquire penetrative observations of the specimen from a variety of perspectives; these are then used as input to a mathematical procedure that produces a reconstructed "volume image" of all or part of the interior of the specimen. In order to achieve a series of different lines of sight as alluded to here, one can, for example, choose to: (i) keep the source and detector static and move the specimen relative to them, (ii) keep the specimen static and move the source relative to it, or (iii) use a static, distributed array of sources/detectors in conjunction with a static specimen invoking different source/detector pairs along different lines of sight, either serially or concurrently.

In embodiments where the specimen is kept static, one can elect to (a) move the detector in synchronization with the source; (b) embody the detector as a static or moving array of sub-detectors, with positions matched to correspond to the different positions to be assumed by the source.

Regardless of whether the source or specimen is moved, it is possible to describe their relative motion using, for example, a specimen-centric coordinate system and/or reference frame. Typically, use is made of: (i) a circular scan, in which the source follows a planar orbit about the specimen, and images are captured at a relatively high sampling rate (i.e. quasi-continuously) along this orbit. This type of scan can be applied in situations where only a relatively thin "slice" of a specimen has to be imaged. See, for example, WIKIPEDIA, "Cone Beam Computed Tomography" [online] [retrieved 2017-Oct. 4]; (ii) a helical scan, in which the source follows a coil-like (spiral) path about a (longitudinal) axis of the specimen, and images are again captured at a relatively high sampling rate (i.e. quasi-continuously) along this path. This type of scan can be applied in situations where a relatively elongated portion of a specimen has to be imaged. It is typically achieved by combining circular motion (e.g. of the source) and concurrent translational motion (e.g. of the specimen). See, for example, WIKIPEDIA, "Spiral Computed Tomography," [online] [retrieved 2017-Oct. 4]; or (iii) a "matrix" of sampling points, which are not disposed along a curve, but are instead arranged in a substantially uniform distribution. Such a scenario is set forth in co-pending European Patent Application EP15181202.1/U.S. patent application Ser. No. 15/237,309 (with the same assignee as the present application).

The beam of radiation that traverses the specimen can, for example, be regarded as being cone-like (thus yielding so-called cone beam tomography) or resembling a segment of a disc (thus yielding so-called fan beam tomography), depending on the geometry/shape that the detector "presents" to the source; alternatively, a parallel/collimated beam is also possible. The "line of sight" alluded to here can be regarded as corresponding to an "optical axis" along which the beam (from source through specimen to detector) propagates; it basically corresponds to the position of a central/median/core ray in that beam.

As regards the mathematical reconstruction technique used to produce a tomogram from a series of input images, use can be made of algorithms such as SIRT (Simultaneous Iterative Reconstruction Technique), ART (Algebraic Reconstruction Technique), DART (Discrete ART), SART (Simultaneous ART), MGIR (Multi-Grid Iterative Reconstruction), and many others. See, for example, the summary presented in the publication: REZVANI, N, "Reconstructed Algorithms in Computerized Tomography" (presentation) 2009 [online] University of Toronto [retrieved 2017-Oct. 5].

Tomographic imaging as referred to here can be performed using a standalone apparatus, which is conventionally the case in medical imaging applications, for example, where the specimen (e.g. a human or animal) is macroscopic. Standalone CT tools are also available for performing so-called "micro CT," in which a micro-focused source is used to image microscopic specimens, e.g. in geology/petrology, biological tissue studies, etc. Continuing this drive toward ever-greater resolution, so-called "nano CT" instruments have also been developed; these may be standalone tools, but, for example, they may also be embodied as (add-on) modules for (a vacant vacuum/interface port of) a charged-particle microscope (CPM), in which case the CPM's charged-particle beam is used to irradiate a (block-like) metal target, causing production of the X-rays used to perform the desired tomography. More information on (some) of these topics can, for example, be gleaned from the following references: WIKIPEDIA, "X-ray Microtomography" [online] [retrieved 2017-Oct. 5], WIKIPEDIA, "Nanotomography" [online] [retrieved 2017-Oct. 5], and NEUSER, E and SUPPES, A, "NanoCT® Visualizing Internal 3D Structures with Submicrometer Resolution." International Symposium on Digital Industrial Radiology and Computed Tomography, Jun. 25, 2007 [online] [retrieved 2017-Oct. 5].

It should be noted that, as referred to here in the context of a CPM, the phrase "charged particle" should be broadly construed as encompassing: (i) electrons, as in the case of a Transmission Electron Microscope (TEM), Scanning Electron Microscope (SEM), and Scanning Transmission Electron Microscope (STEM), for instance. See, for example, the following references: WIKIPEDIA, "Electron Microscope," [online] [retrieved 2017-Oct. 5], WIKIPEDIA, "Scanning Electron Microscope," [online] [retrieved 2017-Oct. 5], WIKIPEDIA, "Transmission Electron Microscopy," [online] [retrieved 2017-Oct. 5], and WIKIPEDIA, "Scanning Transmission Electron Microscopy," [online] [retrieved 2017-Oct. 5].

(ii) Ions, which may be positive (e.g. Ga or He ions) or negative. Such ion beams can be used for imaging purposes, but they are also often used for surface modification purposes, e.g. as in the case of Focused Ion Beam (FIB) milling, Ion-Beam-Induced Deposition (IBID), Ion-Beam-Induced Etching (IBIE), etc. See, for example, the following references: WIKIPEDIA, "Focused Ion Beam," [online] [retrieved 2017-Oct. 5], WIKIPEDIA, "Scanning Helium Ion Microscope," [online] [retrieved 2017-Oct. 5], and W. H. Escovitz, T. R. Fox and R. Levi-Setti, *Scanning Transmission Ion Microscope with a Field Ion Source*, Proc. Nat. Acad. Sci. USA 72(5), pp 1826-1828 (1975).

(iii) Other charged particles, such as protons and positrons, for instance. See, for example, the following reference: VARENTSOV, D et al., "First Biological Images with High-Energy Proton Microscopy" (abstract) [online] [retrieved 2017-Oct. 5] retrieved from: PUBMED Database.

It should also be noted that, in addition to imaging and/or surface modification, a charged particle beam in a CPM may also have other functionalities, such as performing spectroscopy, examining diffractograms, etc. The present disclosure will predominantly concern itself with tomography as applied to image microscopic specimens, including specimens that are microscopic sub-portions of larger/macroscopic objects; it therefore is primarily (though not necessarily) concerned with micro- and nano-CT techniques.

Figure 1A:
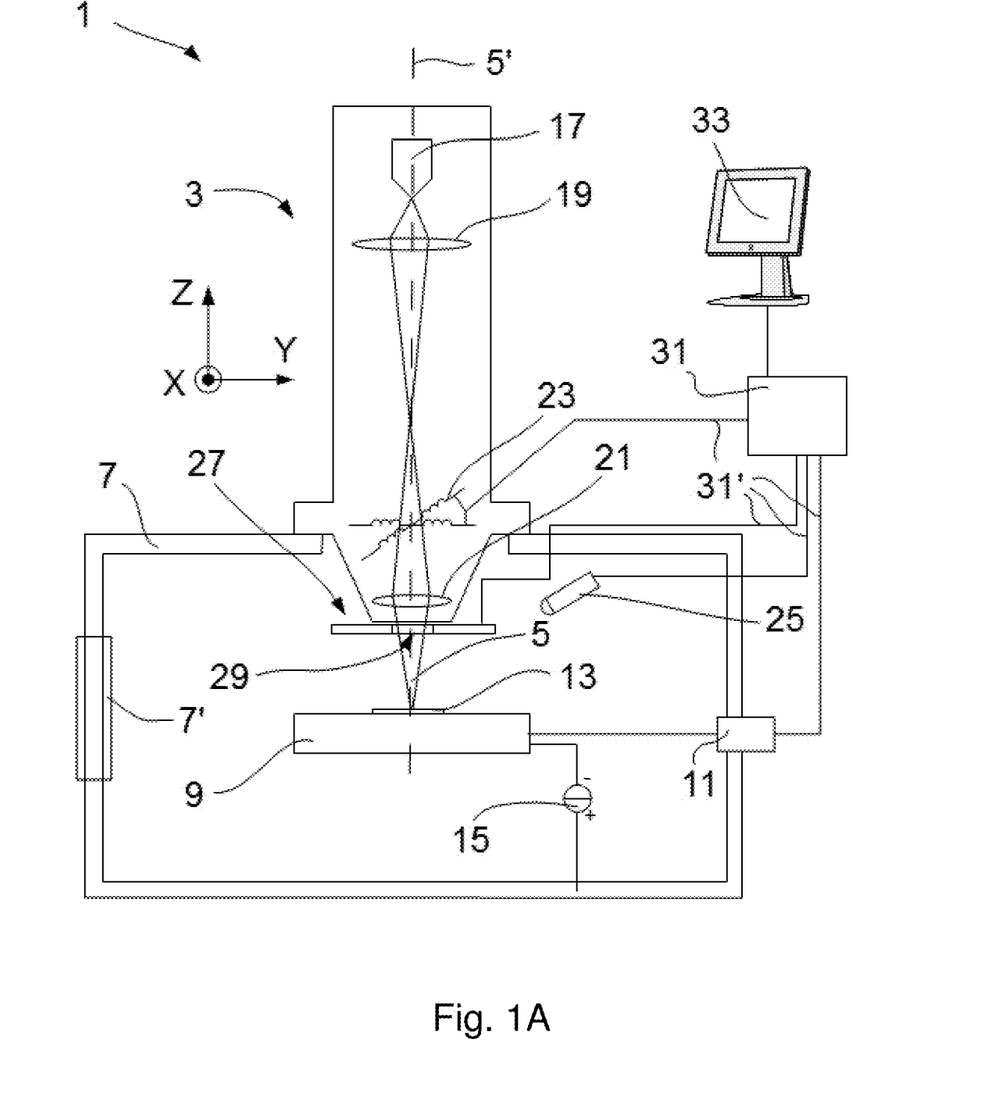
FIG. 1A is a longitudinal cross-sectional elevation of a particular type of CPM in which an embodiment of the current disclosure.
Figure 1B:
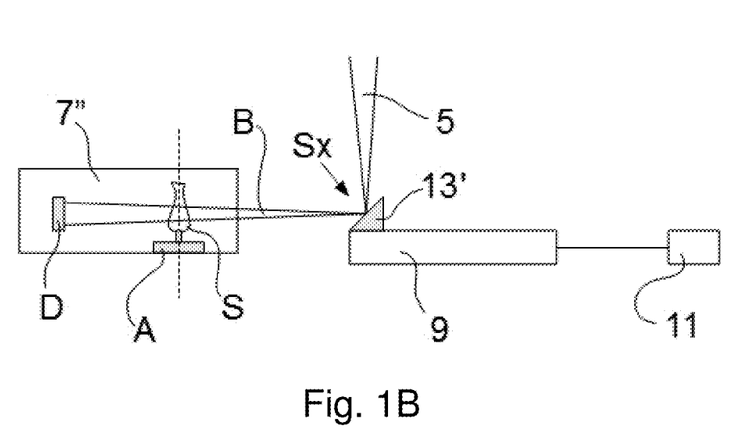
FIG. 1B illustrates a CT module suitable for use in a CPM such as that shown in FIG. 1A.

FIGS. 1A and 1B illustrate aspects of a way of performing a method as set forth in the opening paragraph above, whereby use is made of an in situ (nano-)CT module in a CPM. Referring to FIG. 1B in particular, it is seen how a charged particle beam in a CPM is directed onto a standalone block (13') of metal, where it produces X-rays that are subsequently used to irradiate a specimen (S) under investigation.

It is an object of the disclosure to provide an innovative X-ray tomographic imaging technique. More specifically, it is an object of the disclosure that this new technique should employ a radically different irradiation architecture as compared to known techniques.

These and other objects are achieved in a method as set forth in the opening paragraph above, which method is characterized in that the specimen is disposed within a substantially cylindrical metallic shell with an associated cylindrical axis, a beam of X-rays is produced by directing a beam of charged particles onto a zone of the metallic shell, so as to produce a confined X-ray source at the zone, the series of different lines of sight is achieved by rotating the shell about the cylindrical axis, thereby causing relative motion of the zone relative to the specimen.

The term "cylindrical" as here employed refers to a right circular cylindrical form, i.e. a cylinder with a substantially circular transverse cross-section. The term "metallic" as here employed should be broadly interpreted as encompassing pure metals, metal alloys, metal laminates, metal granulates/aggregates (e.g. metal particles suspended in non-metallic material), and mixtures thereof.

The disclosure has a number of pronounced advantages relative to the prior art. For example, in prior-art micro-CT/nano-CT set-ups using a standalone X-ray target, the cumulative acquisition time for step (d) (i.e. acquiring the series of images from which a tomogram is reconstructed, see opening paragraph above) is relatively long, thereby tending to form a throughput bottleneck in associated process workflows. A major reason for this is the relatively low X-ray intensity that arrives at the specimen from the relatively distal standalone X-ray source. The disclosure manages to move the X-ray source much closer to the specimen, by generating X-rays in the specified cylindrical metallic shell. The separation of the specimen and the X-ray source is thereby determined by the shell radius, which can be very small if desired—e.g. of the order of 10-50 μm, as opposed to (typically) several millimeters/centimeters in situations such as shown in FIG. 1B. As a result of this much smaller separation, the effective source opening angle can be 1-2 orders of magnitude (or more) greater than in prior-art set-ups, with an attendant increase in X-ray intensity and decrease in acquisition time.

Furthermore, the disclosure solves the problem of specimen charging caused by backscattered charged particles. Such backscattered particles will either be electrically impeded by the cylindrical metallic shell acting as a Faraday shield (if grounded) and/or will not be able to physically penetrate the material of the shell. Configuring the X-ray source to be a localized part of a specimen shell means that the specimen cannot positionally drift relative to the X-ray source; this improves measurement stability/reproducibility. By extension, it also removes the prior-art problem of a risk of collision between a standalone X-ray source (anode) and the specimen.

The specimen shell provides ease of confinement and transport of the specimen, since it is de facto encased in its own mini-protective jacket (the shell). Furthermore, it is possible to arrange a number of specimens (in longitudinal succession) in a single (relatively long) shell, greatly improving throughput (by reducing specimen handling/exchange time) when several specimens need to be studied. In addition, it is possible to provide an outer surface of the shell with positional markers, which can be advantageous for alignment and 3D reconstruction purposes, for instance.

The skilled artisan will understand that the metallic shell should comprise material with a relatively high atomic number (high Z), so as to efficiently generate X-rays when irradiated by the charged particle beam. Examples of suitable metals in this context include molybdenum, tungsten, platinum, palladium, gold, etc. (including alloys, laminates and aggregates of such metals).

DETAILED DESCRIPTION

In an embodiment of the disclosure (referred to hereafter as a "type 1 shell"), the metallic shell is a pre-existing cylindrical tube into which the specimen is inserted. Put another way, the shell is an essentially independent structure that is initially empty (in that there is no specimen inside) but into which a specimen of choice is later inserted/mounted. In an alternative embodiment (referred to hereafter as a "type 2 shell"), the shell is deposited (e.g. using sputter-coating, chemical vapor deposition, dipping, etc.) as a skin upon a substantially cylindrical specimen; in this case, the shell is never a "freestanding" structure, but is instead supported by the underlying specimen, onto which it is deposited ex post facto.

In a particular embodiment of the disclosure, the shell is comprised in a composite structure in which a metallic stratum overlies a sub-stratum of non-metallic material. In other words, the shell comprises an outer metallic cladding that is disposed upon an inner non-metallic carrier. This non-metallic sub-stratum can fulfill various possible purposes, including (but not limited to): (i) serving to increase a separation between the localized x-ray source and the specimen, for example to avoid "runaway magnification" associated with (almost) zero source/specimen separation, (ii) serving to create a buffer of low-atomic-number ("low-Z") material between the localized X-ray source and the specimen, so as to deter X-ray generation in the specimen itself, (iii) serving to create a relatively thick and rigid "carrier structure" for a relatively thin and fragile metallic stratum (in the case of a type I shell), and (iv) serving to fill up irregularities in a surface of a specimen before deposition of a metallic stratum thereupon (in the case of a type II shell).

Of course, the inventive shell does not have to be a composite in this manner, and may instead be embodied as a straightforward metallic pipe (type I shell) or a metallic skin deposited directly onto a cylindrical surface of the specimen (type II shell). In the former case, the pipe walls are preferably relatively thin, e.g. of the order of ca. 10-100 μm thick (a higher incoming charged particle beam energy can be used with a thicker pipe wall, if necessary or desired). If a composite structure is chosen, then the sub-stratum can for example, comprise a material selected from the group comprising vitreous material, ceramic material, dielectric material, plastic material, carbon, and combinations thereof. Examples of such materials include various types of glass, quartz, ceramics, silicon carbide, sapphire, diamond, Perspex (PMMA), acrylonitrile butadiene styrene (ABS), nylon, carbon fiber, etc. It deserves mention that a relatively thick metallic pipe (type I shell) as referred to here will tend to produce a lower resolution than a composite structure with a relatively thin metallic stratum because the interaction zone between the charged particle beam and metal is now thicker, and thus larger, but it will also tend to produce a higher X-ray intensity for the same reason. The skilled artisan can himself decide if this tradeoff is attractive in a particular situation—e.g. to do a fast, initial scan of a specimen. It should also be noted that a type II shell or a composite type I shell as referred to here has the advantage of allowing the metallic shell/stratum to be patterned (e.g. as an array of dots, or a series of parallel lines (rings) or other geometric shapes) if desired. Patterning in this way can, for example, be used to produce resolution enhancement effects. Using a composite type I shell is also an easy way of allowing (a selection of) different metals and/or stratum thicknesses to be employed, since the low-Z sub-stratum acts as an inert substrate/carrier on which a wide variety of materials and thicknesses can be applied. In this regard, it is noted that the constitution/thickness of the metallic stratum will affect factors such as the Z-number, X-ray generation efficiency, X-ray brightness and attainable resolution/contrast.

As regards the possible dimensioning of the inventive shell, the skilled artisan will be able to select values that are well-suited to a given situation. To give some guidance in this regard, the following non-limiting values can, for example, be considered for a composite type I shell (sub-stratum tube) used for nano-CT applications: (1) outer diameter: ~50-150 μm, (2) tube wall thickness: ~5-15 μm, (3) thickness of metallic cladding on outer surface of tube: ~0.1-0.2 μm, (4) distance from cylindrical axis to detector surface: ~0.5-1.5 cm, (5) Length (along cylindrical axis): 5-15 mm.

As regards these individual parameters, the skilled artisan will understand that parameter (1) affects the distance from the X-ray source to the specimen. Note that a larger diameter than quoted here (e.g. ~1 mm) might be useful for lower-magnification studies, for example. Parameter (2) affects the structural strength of the tube, and the ease with which it can be handled. Parameter (3) affects the achievable X-ray intensity and resolution. Parameter (4) affects the detector's capture angle, i.e. the relative amount of flux that it captures from the point-source-like interaction X-ray production zone in the metallic shell. This is also determined by the detector area.

In practice, it may be useful to have a collection of different type I shells, with different dimensions and/or material constitutions, and to choose per situation a shell that is best suited to a given scenario.

As regards manners in which the specimen can be disposed, provided, or arranged in a type I shell (with sub-stratum tube) to start off with, there are many different possibilities. For example: (i) drawing a liquid containing the specimen into the tube, and sealing the liquid within the tube. This is, for example, suitable for biological specimens such as cells that float in an aqueous solution. The liquid in question can, for example, be sucked into the tube using a syringe, or drawn in by capillary action. If desired, it can be frozen/vitrified after introduction into the tube; (ii) embedding the specimen within a body of matrix material within the tube, which matrix material is selected from the group comprising resins, gums, gels, pastes, thermosetting fluids, congealing fluids, and combinations thereof. The matrix material in this case simply acts as a supporting mass to keep a relatively small specimen (such as a flake or grain of material) in place. A natural, pre-existing example of such an approach is an archaic bacterium or air bubble trapped in amber; (iii) adhering part of the specimen to an adhesive layer on an inner surface of the tube. A small tweezers or needle (for example) can be used to insert the specimen into the tube and mount it in place; (iv) wedging (stuffing) the specimen between opposed inner walls of the tube. Such an approach can, for example, be used with relatively large specimens that are somewhat compliant, such as a piece of wood, organ tissue, etc. In this case, one could, for example, take a "core" of specimen material into the tube, by pushing an open end of the tube into a mass of such material.

The skilled artisan will be able to choose a specimen preparation and mounting method best suited to the needs of a particular situation. In essence, one will image and mathematically reconstruct a cylindrical volume within the metallic shell, and the specimen of interest, which may be singular or plural/distributed in nature, will be located within this reconstructed volume. Ideally, the specimen is on or near the cylindrical axis, but specimens or specimen parts that are not on-axis can also be reconstructed.

A particular embodiment of the inventive method is such that, supplemental to the rotational motion of the shell and specimen about its cylindrical axis, there is also relative motion of the charged particle beam with respect to the shell in a direction parallel to said cylindrical axis. Such parallel motion may be achieved by moving the shell and/or the charged particle beam in a direction that has at least a component parallel to said axis. In this way, one can achieve a helical scan path, or a distributed matrix of sampling points as alluded to above, for example. It should be noted that both the rotational motion and the translational motion referred to here and elsewhere in this text may be continuous or discrete, incremental, or step-like, as desired.

As regards the rotational motion of the shell about its cylindrical axis, this can, for example, be achieved by mounting the shell to a rotatable chuck having a jaw that closes upon and clamps an extremity of the tube in such a way that the shell's cylindrical axis coincides with a rotational axis of the chuck. This is, for example, analogous to the way in which the chuck of an electric drill grips and rotates a drill bit. As an alternative to the use of such a jaw, one could instead adhere the shell to the chuck using a blob of adhesive, for example.

It should be noted that the charged particle beam used to irradiate the metallic shell may be directed perpendicular thereto (normal incidence) or at an angle to the normal (oblique incidence), according to choice; in the latter case, the metallic shell may, for example, be patterned (rather than bland/continuous) so as to improve attainable resolution.

The disclosure will now be elucidated in more detail on the basis of exemplary embodiments and the accompanying schematic drawings, in which:

In the Figures, corresponding features may be denoted using corresponding reference symbols.

EXAMPLES

FIG. 1A is a highly schematic depiction of an embodiment of a CPM 1 that can be used in conjunction with the present disclosure and/or with prior-art X-ray tomography techniques; more specifically, it shows an embodiment of a SEM—though, in the present context, it could just as validly be an ion-based microscope, for example, or a TEM, for instance. The microscope 1 comprises a particle-optical column/illuminator 3, which produces a beam 5 of charged particles (in this case, an electron beam) that propagates along a particle-optical axis 5'. The particle-optical column 3 is mounted on a vacuum chamber 7, which comprises a specimen carrier 9 and associated stage/actuator 11 for holding/positioning a specimen 13. The vacuum chamber 7 is evacuated using vacuum pumps (not depicted). With the aid of voltage source 15, the specimen carrier 9, or at least the specimen 13, may, if desired, be biased (floated) to an electrical potential with respect to ground.

The particle-optical column 3 comprises an electron source 17 (such as a Schottky emitter), electrostatic/magnetic lenses 19, 21 (in general, more complex in structure than the schematic depiction here) to focus the electron beam 5 onto the specimen 13, and a deflection unit 23 to perform beam deflection/scanning of the beam 5. When the beam 5 impinges on or is scanned across the specimen 13, it will precipitate emission of various types of "stimulated" radiation, such as backscattered electrons, secondary electrons, X-rays and cathodoluminescence (infra-red, visible and/or ultra-violet photons); one or more of these radiation types can then be sensed/recorded using one or more detectors, which may form an image, spectrum, diffractogram, etc., typically by assembling a "map" (or "matrix") of detector output as a function of scan position on the specimen. The present Figure shows two such detectors, 25, 27, which may, for example, be embodied as follows. Detector 25 may, for example, be an electron detector (such as an Solid State Photo-Multiplier or Everhart-Thornley detector), a (cathodoluminescence) light detector (such as a photodiode), or an X-ray detector (such as an SDD or Si(Li) sensor). Detector 27 may be a segmented electron detector, comprising a plurality of independent detection segments (e.g. quadrants) disposed about a central aperture 29 (allowing passage of the beam 5). Such a detector can, for example, be used to investigate (the angular dependence of) a flux of output (secondary or backscattered) electrons emerging from the specimen 13. These are just examples, and the skilled artisan will understand that other detector types, numbers and geometries/configurations are possible.

The microscope 1 further comprises a controller/computer processing unit 31 for controlling inter alia the lenses 19 and 21, the deflection unit 23, and detectors 25, 27, and displaying information gathered from the detectors 25, 27 on a display unit 33 (such as a flat panel display); such control occurs via control lines (buses) 31'. The controller 31 (or another controller) can additionally be used to perform various mathematical processing, such as combining, integrating, subtracting, false colouring, edge enhancing, and other processing known to the skilled artisan. In addition, automated recognition processes (e.g. as used for particle analysis) may be included in such processing.

Also depicted is a vacuum port 7', which may be opened so as to introduce/remove items (components, specimens) to/from the interior of vacuum chamber 7, or onto which, for example, an ancillary device/module may be mounted (not depicted). A microscope 1 may comprise a plurality of such ports 7', if desired.

In the context of performing X-ray tomography, the microscope 1 can also comprise an in situ CT module 7" as shown in FIG. 1B. In this figure, the CPM's specimen carrier 9 has been provided with a standalone metal target 13', which is positioned (using actuator 11) so that electron beam 5 impinges upon it, thus producing X-rays in a variety of directions. The Figure shows a beam B of such X-rays that propagate to one side from target 13' (effective source Sx) into module 7", where they pass through a specimen S and impinge upon a detector D. The specimen S is mounted on a stage apparatus A that allows the specimen S to be positioned/moved (typically translated and rotated) relative to the source Sx. Such a CT module 7" may be permanently present (ab initio) in the vacuum enclosure 7, or it may be an add-on module that can be mounted (post-manufacture of the CPM 1) on/within a spare vacuum port 7', for example.

Embodiment 1

Figure 2A:
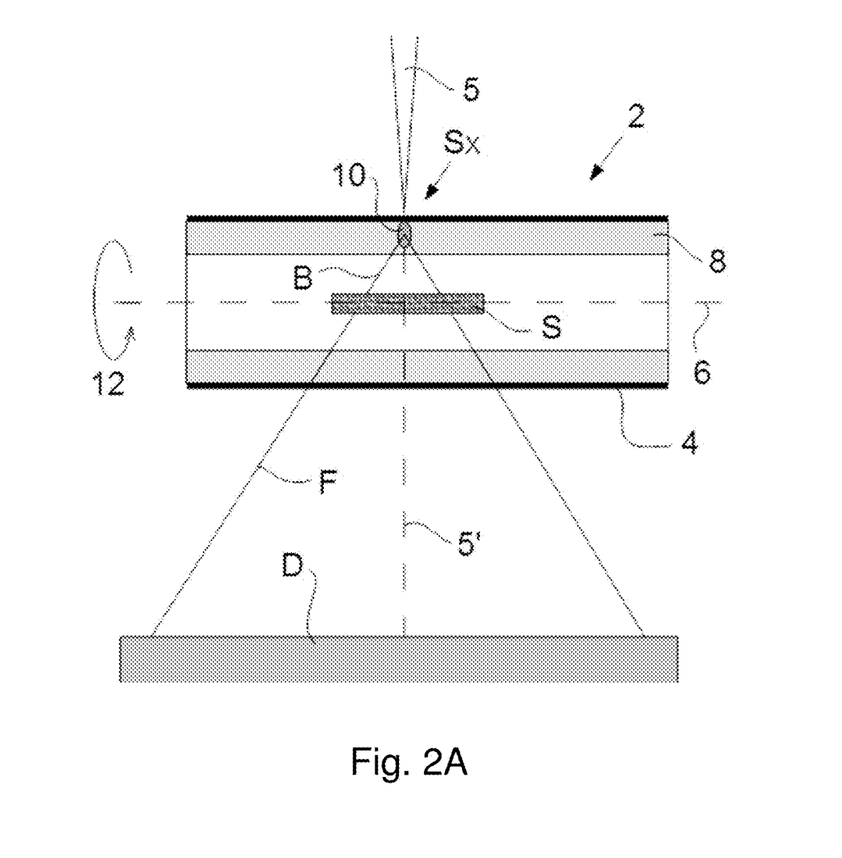
FIG. 2A shows an embodiment of a type I shell according to the present disclosure.

FIG. 2A shows an embodiment of a type I shell according to the present disclosure. The shell 2 is comprised in a composite structure in which a hollow tube 8 (sub-stratum) carries a cylindrical metallic cladding 4 (stratum) that is centered on a cylindrical axis 6; as here depicted, a specimen S is disposed within said tube 8. The tube 8 comprises low-Z material (such as glass). Exemplary dimensions of the depicted tube 8 are (approximately): Outer diameter: 100 µm, wall thickness: 10 µm, thickness of metallic stratum: 0.1 µm, length (parallel to axis 6): 5 mm.

Also shown is a focused beam 5 of charged particles (e.g. electrons) impinging onto/into a zone 10 of the metallic stratum 4, so as to produce a confined X-ray source Sx at said zone 10. This X-ray source Sx in turn irradiates the specimen S with an X-ray beam B, causing a flux F of X-rays to emerge from the specimen S and land on detector D. The incoming charged particle beam 5 propagates along axis/line-of sight 5'. According to the disclosure, a series of different such lines of sight 5' is achieved by rotating the tube 8 (including cladding 4 and specimen S) about its cylindrical axis 6 (see arrow 12), thereby causing relative motion of zone 10 and source Sx relative to the specimen S. If desired, supplemental relative motion of tube 8 and beam 5 can also be effected parallel to axis 6.

Figure 2B:
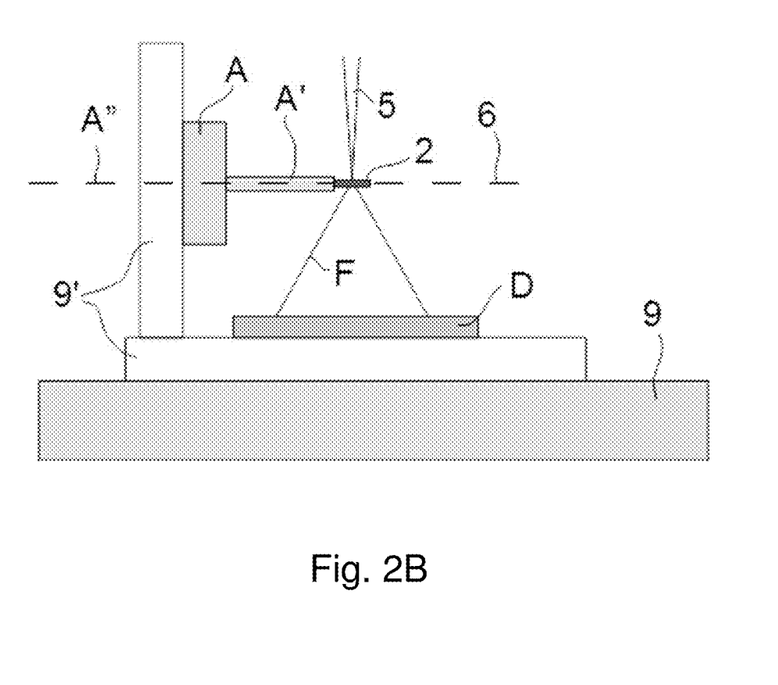
FIG. 2B illustrates how a shell such as that in FIG. 2A can be rotated in accordance with the present disclosure.

FIG. 2B illustrates how a shell 2 such as that in FIG. 2A can be rotated in accordance with the present disclosure. As here depicted, the specimen carrier 9 of a CPM 1 (see FIG. 1A) is provided with a (mountable/demountable) frame 9' on which is mounted an actuator A that is (at least) capable of producing rotary motion of a chuck A' about rotary axis A". The narrow/fine chuck A' can hold onto an extremity/end of shell 2 (tube 8) using a jaw/pincer member (not depicted), or a drop of adhesive, for example. The shell 2 is thus mounted on the chuck A' that the cylindrical axis of the former corresponds with the rotational axis of the latter. The distance from axis 6 to detector D is, for example, of the order of 1-2 cm.

The charged particle beam can, for example, have a beam current of ca. 0.1-10 µA and a beam energy of 30 keV, and be focused to a spot size of ca. 50 nm-1 µm. The skilled artisan will be able to make his own choices in this regard.

Embodiment 2

As an alternative to the situation depicted in FIG. 2A, a metallic shell could be deposited as a skin upon an outer surface of a substantially cylindrical specimen S—either directly or upon a pre-applied sub-stratum of low-Z material—thereby producing a type II shell.

In view of the many possible embodiments to which the principles of the disclosed disclosure may be applied, it should be recognized that the illustrated embodiments are only preferred examples of the disclosure and should not be taken as limiting the scope of the disclosure. Rather, the scope of the disclosure is defined by the following claims. We therefore claim as our disclosure all that comes within the scope and spirit of these claims.

We claim:

1. A method of investigating a specimen using X-ray tomography, comprising:
   (a) mounting a specimen to a specimen holder;
   (b) irradiating the specimen with a beam of X-rays along a first line of sight through the specimen;
   (c) detecting a flux of X-rays transmitted through the specimen and forming a first image;
   (d) repeating steps (b) and (c) for a series of different lines of sight through the specimen, thereby producing a corresponding series of images; and
   (e) performing a mathematical reconstruction on the series of images, so as produce a tomogram of at least part of the specimen;
   wherein the specimen is disposed within a substantially cylindrical metallic shell with an associated cylindrical axis and the beam of X-rays is produced by directing a beam of charged particles onto a zone of the metallic shell so as to produce a confined X-ray source at the zone; and
   wherein the series of different lines of sight is achieved by rotating the metallic shell about the cylindrical axis, thereby causing relative motion of said zone relative to the specimen.

2. The method of claim 1, wherein the metallic shell comprises a pre-existing cylindrical tube into which the specimen is inserted.

3. The method of claim 2, wherein the specimen is disposed within the pre-existing cylindrical tube using a technique selected from the group comprising: (a) drawing a liquid containing the specimen into the tube, and sealing the liquid within the tube; (b) embedding the specimen within a body of matrix material within the tube wherein the matrix material is selected from the group comprising resins, gums, gels, pastes, thermosetting fluids, congealing fluids, and combinations thereof; (c) adhering part of the specimen to an adhesive layer on an inner surface of the tube; (d) wedging the specimen between opposed inner walls of the tube, and combinations thereof.

4. The method of claim 2, wherein the metallic shell has an outer diameter less than 1.5 mm.

5. The method of claim 2, wherein the metallic shell has an outer diameter less than 500 µm.

6. The method of claim 2, wherein the metallic shell has an outer diameter in the range 50-150 µm.

7. The method of claim 1, wherein the specimen is substantially cylindrical in form and wherein the metallic shell is deposited as a skin upon a cylindrical surface of the specimen.

8. The method of claim 7, wherein the metallic shell has an outer diameter less than 500 µm.

9. The method of claim 7, wherein the metallic shell has an outer diameter in the range 50-150 µm.

10. The method of claim 1, wherein the metallic shell comprises a composite structure in which a metallic stratum overlies a sub-stratum of non-metallic material.

11. The method of claim 10, wherein the sub-stratum comprises a material selected from the group comprising vitreous material, ceramic material, dielectric material, plastic material, carbon, and combinations thereof.

12. The method of claim 10, wherein the metallic shell has an outer diameter less than 500 µm.

13. The method of claim 10, wherein the metallic shell has an outer diameter in the range 50-150 µm.

14. The method of claim 1, wherein the metallic shell has an outer diameter less than 1.5 mm.

15. The method of claim 1, wherein the metallic shell has an outer diameter less than 500 µm.

16. The method of claim 1, wherein the metallic shell has an outer diameter in the range 50-150 µm.

17. The method of claim 1, wherein the step of rotating the metallic shell about the cylindrical axis further comprises moving the charged particle beam with respect to the metallic shell in a direction parallel to the cylindrical axis.

18. The method of claim 1, wherein the rotation of the metallic shell is achieved by mounting the shell to a rotatable chuck having a jaw that closes upon and clamps an extremity of the shell such that the cylindrical axis coincides with a rotational axis of the chuck.

19. The method of claim 1, wherein the charged particle beam is directed onto the metallic shell at a non-perpendicular angle.

20. The method of claim 1, in which the metallic shell is patterned.

* * * * *